(12) United States Patent
Vreeman et al.

(10) Patent No.: US 7,632,302 B2
(45) Date of Patent: Dec. 15, 2009

(54) STENT AND STENT DELIVERY SYSTEM FOR OSTIAL LOCATIONS IN A CONDUIT

(75) Inventors: Daniel J. Vreeman, Rogers, MN (US); Joshua Evans Berman, Shoreview, MN (US); Richard Kusleika, Eden Prairie, MN (US); Steve Gene Zaver, Plymouth, MN (US); Lixiao Wang, Long Lake, MN (US)

(73) Assignee: ev3 Inc., Plymouth, MN (US)

( * ) Notice: Subject to any disclaimer, the term of this patent is extended or adjusted under 35 U.S.C. 154(b) by 199 days.

(21) Appl. No.: 11/559,455

(22) Filed: Nov. 14, 2006

(65) Prior Publication Data
US 2007/0129785 A1    Jun. 7, 2007

Related U.S. Application Data

(60) Provisional application No. 60/736,585, filed on Nov. 14, 2005.

(51) Int. Cl.
*A61F 2/06*  (2006.01)
(52) U.S. Cl. .................................. 623/1.16; 623/1.15
(58) Field of Classification Search ....... 623/1.11–1.36; 606/108
See application file for complete search history.

(56) References Cited

U.S. PATENT DOCUMENTS

| 4,768,507 A | 9/1988 | Fischell et al. |
| 5,064,435 A | 11/1991 | Porter |
| 5,147,370 A | 9/1992 | McNamara et al. |
| 5,246,445 A | 9/1993 | Yachia et al. |
| 5,372,600 A | 12/1994 | Beyar et al. |
| 5,607,444 A | 3/1997 | Lam |
| 5,632,762 A | 5/1997 | Myler |
| 5,695,499 A | 12/1997 | Helgerson et al. |
| 5,749,890 A | 5/1998 | Shaknovich |
| 5,868,777 A | 2/1999 | Lam |
| 5,925,062 A | 7/1999 | Purdy |

(Continued)

FOREIGN PATENT DOCUMENTS

EP        1 138 280 A2     10/2001

(Continued)

OTHER PUBLICATIONS

Han, Y. et al., "Flared Polyurethane-covered Self-expandable Nitinol Stent for Malignant Biliary Obstruction," J. Vasc. Interv. Radiol., vol. 14, No. 10, pp. 1291-1301 (Oct. 2003).

(Continued)

*Primary Examiner*—Suzette J Gherbi
(74) *Attorney, Agent, or Firm*—Rissman Hendricks & Oliverio, LLP

(57) ABSTRACT

A renal stent includes a balloon expandable segment intended for deployment in the renal vessel and a self expanding segment intended for deployment in the aortic segment. One or both of the balloon expandable and self expanding segments can be deployed in the ostial region of the renal vessel, typically the renal artery. The balloon expandable segment provides superior radial strength for maintaining dilated diameter of the renal vessel. The self expanding segment expands to conform to the flared ostial and aortic regions of the vessel. The self expanding segment can be balloon dilated to enhance conformance of the self expanding stented segment to the ostial and aortic regions.

6 Claims, 10 Drawing Sheets

U.S. PATENT DOCUMENTS

| | | | |
|---|---|---|---|
| 5,980,532 A * | 11/1999 | Wang | 623/1.11 |
| 6,096,071 A | 8/2000 | Yadav | |
| 6,132,460 A | 10/2000 | Thompson | |
| 6,132,461 A | 10/2000 | Thompson | |
| 6,203,569 B1 | 3/2001 | Wijay | |
| 6,290,728 B1 | 9/2001 | Phelps et al. | |
| 6,358,274 B1 | 3/2002 | Thompson | |
| 6,945,994 B2 | 9/2005 | Austin et al. | |
| 6,969,402 B2 | 11/2005 | Bales et al. | |
| 7,037,327 B2 | 5/2006 | Salmon et al. | |
| 7,105,015 B2 | 9/2006 | Goshgarian | |
| 7,288,111 B1 * | 10/2007 | Holloway et al. | 623/1.15 |
| 2001/0027388 A1 | 10/2001 | Greenberg | |
| 2003/0105516 A1 | 6/2003 | Austin | |
| 2003/0114917 A1* | 6/2003 | Holloway et al. | 623/1.13 |
| 2004/0093058 A1* | 5/2004 | Cottone et al. | 623/1.11 |
| 2004/0186555 A1 | 9/2004 | Bonsignore et al. | |
| 2004/0260378 A1 | 12/2004 | Goshgarian | |
| 2005/0137680 A1 | 6/2005 | Ortiz et al. | |
| 2006/0025849 A1* | 2/2006 | Kaplan et al. | 623/1.15 |
| 2007/0112411 A1* | 5/2007 | Obermiller et al. | 623/1.13 |
| 2007/0213803 A1* | 9/2007 | Kaplan et al. | 623/1.11 |

FOREIGN PATENT DOCUMENTS

| | | |
|---|---|---|
| WO | WO 99/36015 | 7/1999 |
| WO | WO 2005/032424 A1 | 4/2005 |
| WO | WO 2005/102181 A1 | 11/2005 |

OTHER PUBLICATIONS

Shin, J. et al., "Malignant Tracheobronchial Strictures: Palliation with Covered Retrievable Expandable Nitonol Stent," J. Vasc. Interv. Radiol., vol. 14, No. 12, pp. 1525-1534 (Dec. 2003).

Vivas, I. et al., "Percutaneous Extrahepatic Portacaval Shunt with Covered Prostheses: Feasibility Study," J. Vasc. Interv. Radiol., vol. 14, No. 12, pp. 1543-1552 (Dec. 2003).

* cited by examiner

STENT AND STENT DELIVERY SYSTEM FOR OSTIAL LOCATIONS IN A CONDUIT

FIELD OF THE INVENTION

The present invention relates to luminal implants, and, more particularly, to stents for use in treating vascular disease.

BACKGROUND OF THE INVENTION

Stents are widely used for supporting a lumen structure in a patient's body. For example, a stent may be used to maintain patency of a coronary artery, other blood vessel or other body lumen such as the ureter, urethra, bronchus, esophagus, or other passage. A stent is typically a metal, tubular structure, although polymer stents are known. Stents can be permanent enduring implants, or can be bioabsorbable at least in part. Bioabsorbable stents can be polymeric, bio-polymeric, ceramic, bio-ceramic, or metallic, and may elute over time substances such as drugs.

In certain stent designs, the stent is an open-celled tube that is expanded by an inflatable balloon at the deployment site. Another type of stent is of a "self-expanding" type. A self-expanding stent does not use a balloon or other source of force to move from a collapsed state to an expanded state. A self-expanding stent is passed through the body lumen in a collapsed state. At the point of an obstruction, or other deployment site in the body lumen, the stent is expanded to its expanded diameter for its intended purpose. An example of a self-expanding stent is a coil structure that is secured to a stent delivery device under tension in a collapsed state. At the deployment site, the coil is released so that the coil can expand to its enlarged diameter. Coil stents can be manufactured using a variety of methods, such as winding of wire, ribbon, or sheet on a mandrel or by laser cutting from a tube, followed by the appropriate heat treatments. Another type of self expanding stent is an open-celled tube made from a self-expanding material, for example, the Protégé GPS stent from ev3, Inc. of Plymouth, Minn. Open cell tube stents are commonly made by laser cutting of tubes, or cutting patterns into sheets followed by or preceded by welding the sheet into a tube shape, and other methods.

The shape, length and other characteristics of a stent are typically chosen based on the location in which the stent will be deployed. However, selected segments of the human vasculature present specific challenges due to their shape and configuration. One such situation involves the ostium of short renal arteries within the human body.

Conventional stents are generally designed for segments of long cylindrical vessels. When such stents are deployed at the ostium of short renal arteries, in an attempt to prevent further progression of arteriosclerosis disease from aorta into renals, they may extend into the aorta and disrupt the normally laminar blood flow. This result further compounds an existing need to minimize disruption of the flow pattern at the ostium. In addition, stents are hard to position on a consistent basis at the precise ostial location desired, and placement of renal stents can release arteriosclerotic debris from the treatment area. Such debris will flow distally into the kidney and embolize, causing impaired renal function.

Accordingly, it is desirable to flare the end of a stent to minimize disruption to flow pattern at ostium and to simplify re-access in the future. However, existing stents are hard to flare with existing expansion means. Stents suitable for expansion of renal arteries must have high radial strength when expanded to resist vessel forces tending to radially collapse the stent. This need for high stent strength makes suitable stents difficult to flare. A stent configuration designed to address these concerns is disclosed in commonly assigned U.S. patent application Ser. No. 10/816,784, filed Apr. 2, 2004, by Paul J. Thompson and Roy K. Greenberg, US Publication Number US 2004/0254627 A1. However, the stent, when flared, has a lower percentage of coverage of vessel wall at flared regions than is desirable. It is known that stent struts, when expanded into contact with the vessel wall, should cover a certain percentage of the internal vessel wall area in order to prevent prolapse of tissue through the open spaces between stent struts.

Accordingly, a need exists for a stent that can be placed at the renal ostium which is both strong and provides a high percentage of vessel wall coverage.

Further need exists for a stent that will minimize disruption of the flow pattern at the ostium and which will lower the risk of embolization during deployment.

SUMMARY OF THE INVENTION

According to one aspect of the present invention, a renal stent comprises a balloon expandable segment which is deployed in the renal vessel and a self expanding segment which is deployed in the aortic segment. Either or both of the balloon expandable and self expanding segments can be deployed in the ostial region of the renal vessel, typically the renal artery. The balloon expandable segment provides superior radial strength for maintaining dilated diameter of the renal vessel. The self expanding segment expands to conform to the flared ostial and aortic regions of the vessel. The self expanding segment can be balloon dilated to enhance conformance of the self expanding stented segment to the ostial and aortic regions.

According to one aspect of the present invention, a stent for insertion into a body lumen comprises a first tubular, self-expanding section; a second tubular, balloon-expandable section; and a mechanism for limiting axial movement of the first and second tubular sections relative to each other.

According to a second aspect of the present invention, a stent for insertion into a body lumen comprises a tube formed of a uniform material having i) a first section to which a first process is applied, and ii) a second section to which a second process is applied; and wherein the expansion characteristics of the first and second sections within the body lumen are different.

According to a third aspect of the present invention, a stent for insertion into a body lumen comprising a plurality of sections, each section defining a plurality of cells, each cell at least partially defined by a plurality of struts, selected of the struts in each section connecting to struts of an adjacent stent section, wherein the number of connecting struts between adjacent segments increases proximally.

According to a fourth aspect of the present invention, system for delivering a medical device within a body lumen comprises: a tubular catheter having proximal and distal ends and comprising an outer shaft member slidably disposed about an inner shaft member; first and second balloons carried at a distal end of inner shaft member; a medical device comprising i) a first tubular, balloon-expandable section; and ii) a second tubular, self-expanding section; and wherein the first section of the medical device is disposed intermediate the first balloon and the outer shaft member, and wherein the second section of the medical device is disposed intermediate the second balloon and outer shaft member.

According to a fifth aspect of the present invention, a method for placement of a medical device within a body lumen comprises: disposing a delivery system within the body lumen, the delivery system comprising: a tubular catheter having an outer shaft member slidably disposed about an inner shaft member; first and second balloons carried at a distal end of inner shaft member; a medical device comprising: i) a first balloon-expandable section disposed intermediate the first balloon and the outer shaft member, and a second self-expanding section disposed intermediate the second balloon and outer shaft member. The method further comprises withdrawing the outer shaft member proximally to expose the first balloon-expandable section of the medical device to the body lumen; inflating the first balloon to expand the first section of the medical device against the body lumen; withdrawing the outer shaft member proximally to expose the second self-expanding section of the medical device to the body lumen; and inflating the second balloon to expand the second section of the medical device at least partially against the body lumen.

BRIEF DESCRIPTION OF THE DRAWINGS

The above and further advantages of the invention may be better understood by referring to the following description in conjunction with the accompanying drawings in which.

DETAILED DESCRIPTION

Figure 1:
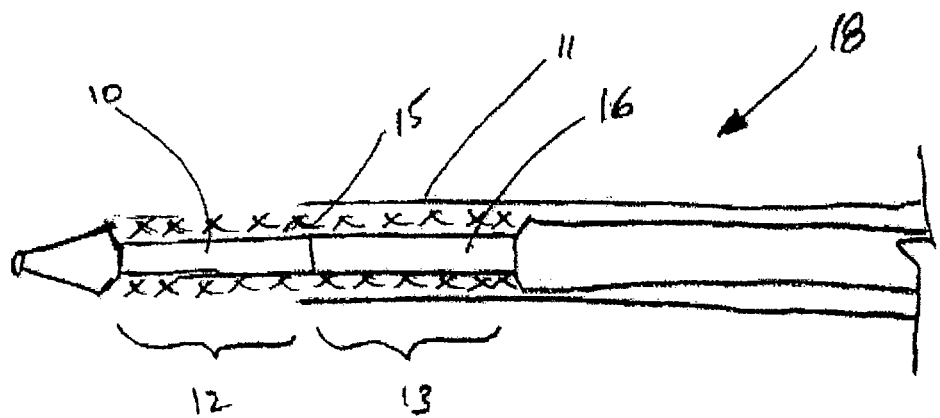
FIGS. 1-4 illustrate conceptually a partial cross-sectional diagram of a stent and a plan view of a stent delivery system in accordance with the present invention.
Figure 2:
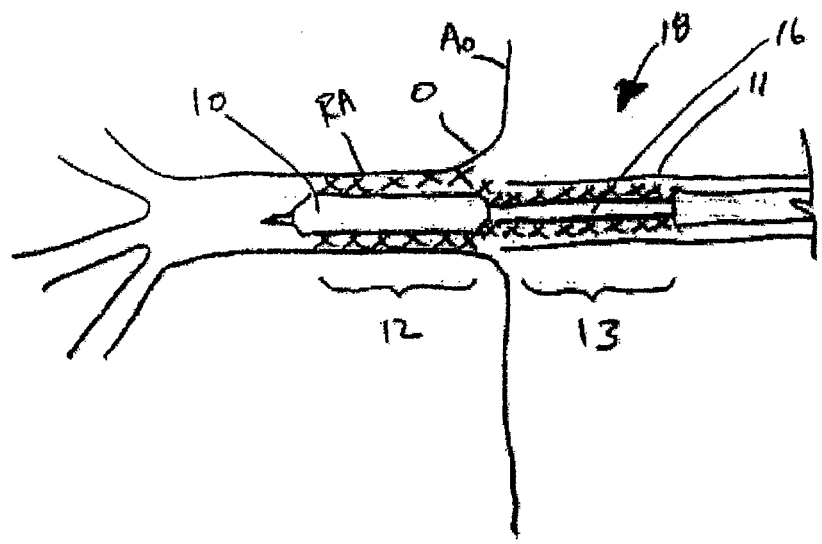
Figure 3:
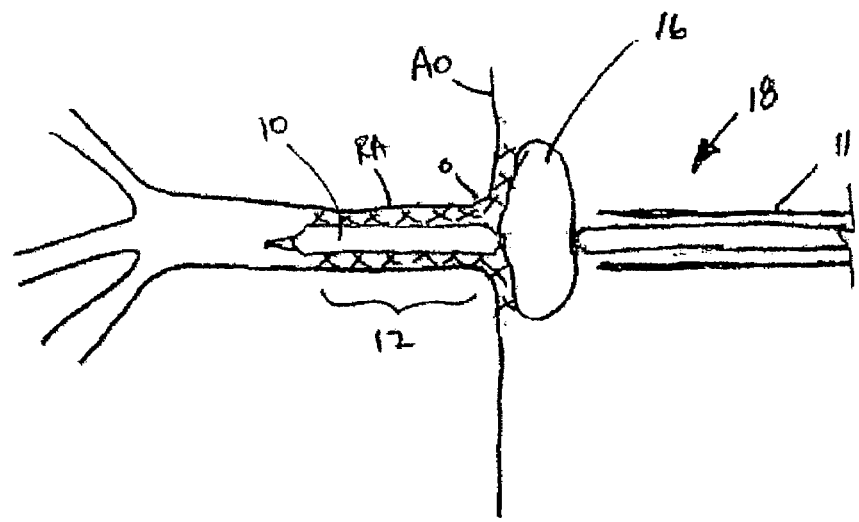
Figure 4:
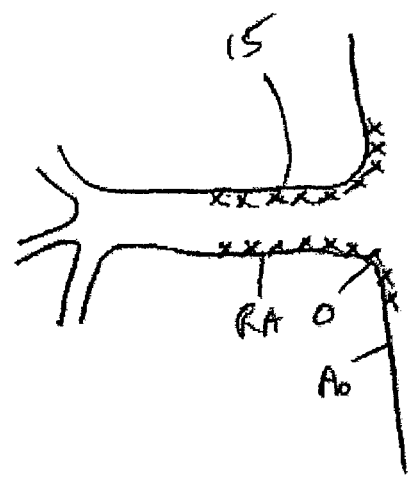

FIG. 1 illustrates a stent 15 in accordance with the present invention. Stent 15 comprises a balloon expandable stent segment 12 and a self expanding stent segment 13. Balloon expandable stent segment 12 may comprise stainless steel alloys, cobalt chrome alloys, titanium, tantalum, platinum, gold, or other materials or their alloys as are known in the art. The self expanding stent segment 13 may be comprise high elastic limit materials such as Elgiloy, cobalt chrome alloys, or other materials as are known in the art. The self expanding stent may comprise so-called shape-memory metals such as nitinol. Shape-memory metal stents can self-expand when thermo mechanically processed to exhibit superelastic material properties. Such shape-memory stents can also self-expand through use of a pre-programmed shape memory effect. Stents processed to exhibit a shape memory effect experience a phase change at the elevated temperature of the human body. The phase change results in expansion of the stent from a collapsed state to an enlarged state FIGS. 1-4 show delivery of the inventive stent 15 to a treatment site. In use, the renal stent 15 is delivered to the treatment site, typically a renal artery, on a catheter 18 with both an outer sheath 11 coaxially retractable from inner balloons 10, 16, as illustrated in FIG. 1. The outer sheath 11 constrains at least the self expandable segment 13 of the stent 15. Distal balloon 10 is used to expand the balloon expandable segment 12 of the stent 15. Optional proximal balloon 16 may be used to dilate the self expanding segment 13 of stent 15. At the treatment site, distal balloon 10 is inflated to expand the balloon expandable segment 12 and dilate the artery RA, thereby fixing the stent at the treatment site, as illustrated in FIG. 2. Outer sheath 11 is then withdrawn, preferably before deflation of distal balloon 10, and self expanding segment 13 diametrically enlarges and conforms to the typically flared ostial O and/or aortic Ao regions near the vessel, as illustrated in FIG. 3. Optionally, the flared portion of the stent 15, that is the portion of the stent 15 opposite the ostial O and aortic Ao regions, can be further dilated with proximal balloon 16. Inflated distal balloon 10 helps to axially anchor catheter 18 in vessel RA so that proximal balloon 16 can deliver force to self expandable stent segment 13 and thereby enhance stent segment 13 apposition to ostial and aortic regions of the vessel. Balloons 10 and 16 are then deflated. Optionally the outer sheath 11 is advanced relative to balloons 10 and 16 to cover the balloons in whole or in part, and the stent delivery catheter 18 is withdrawn from the treatment site, as illustrated in FIG. 4. It is not necessary to position balloon expandable stent segment 12 in the vessel RA with precision because subsequent expansion of the self expanding stent segment 13 will assure continuous coverage of the vessel wall in regions RA, O, and Ao. Stenting of the vessel RA, ostium O, and aorta Ao is accomplished by delivery of one stent to the region thereby reducing the amount of debris generated during stenting as compared to procedures involving delivery of multiple devices.

Figure 5:
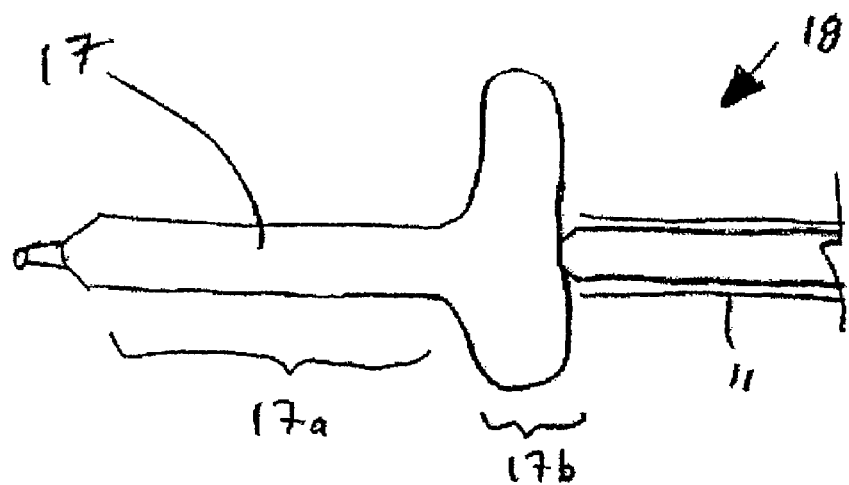
FIG. 5 illustrates conceptually an alternate embodiment of the delivery system of FIGS. 1-4.

FIG. 5 shows an alternate embodiment of a delivery system 18' shown in FIGS. 1-4. In most respects the delivery system shown in FIG. 5 is used in a manner similar to that described above in conjunction with FIGS. 1-4. In this embodiment, balloon 17 provides the function of both balloons 10 and 16 of delivery system 18'. With sheath 11 covering self expanding stent segment 13 and balloon portion 17b, balloon portion 17a is used to dilate balloon expandable stent segment 12. Subsequently, balloon 17 is deflated to a pressure low enough to proximally withdraw sheath 11 until it no longer covers self expanding stent segment 13 and balloon portion 17b. Next, balloon 17 is inflated, causing balloon portion 17a to anchor catheter 18 in the vessel and causing balloon portion 17b to further dilate self expanding stent portion 13. In this embodiment, balloon 17 may be constructed from appropriate materials so as to have differing compliance characteristics between sections 17a and 17b at the same inflation pressure, or, balloon 17 may be formed to assume a profile similar to that illustrated in FIG. 5.

Figure 6:
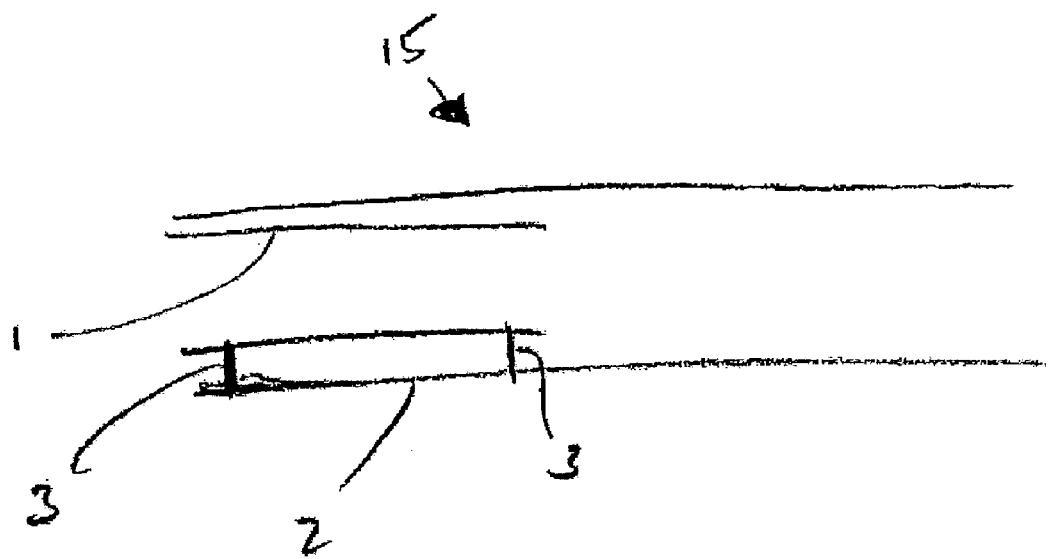
FIG. 6 illustrates conceptually a cross-sectional diagram of another embodiment of a stent in accordance with the present invention.

FIG. 6 illustrates another embodiment of the inventive stent 15 in which the stent segments are at least partially coextensive. In an illustrative embodiment, the balloon expandable segment 1 disposed within the self expanding segment 2, as shown. Alternatively, the balloon expandable segment 1 can be arranged outside of the self expanding segment 2 (not shown). The balloon expandable and self expandable segments may be attached to each other so as to limit axial motion of one segment relative to the other. The stent segments can be attached to one another using means 3 known in the art, including, but not limited to, mechanical interlock, welding, adhesive bonding, over molding, sintering, diffusion bonding, cladding, explosive bonding, ultrasonic welding. If more than one attachment site is required, stent segments 1 and 2 may have matched axial shortening or lengthening during expansion to prevent detachment of attachment sites of means 3. Alternatively, stent segments 1 and 2 can have mis-matched axial shortening or lengthening during expansion provided the attachment sites of means 3 are designed to accommodate such mis-match without becoming detached.

Figure 7:
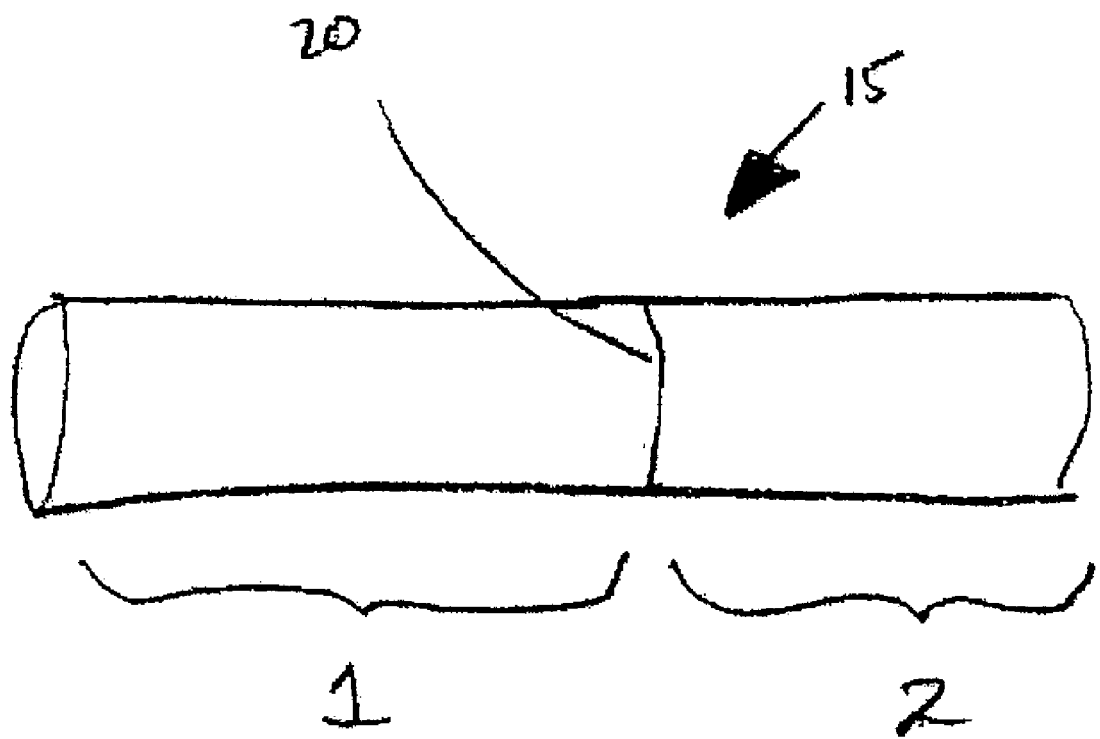
FIG. 7 illustrates conceptually a plan view of an alternative embodiment of a stent in accordance with the present invention.
Figure 8:
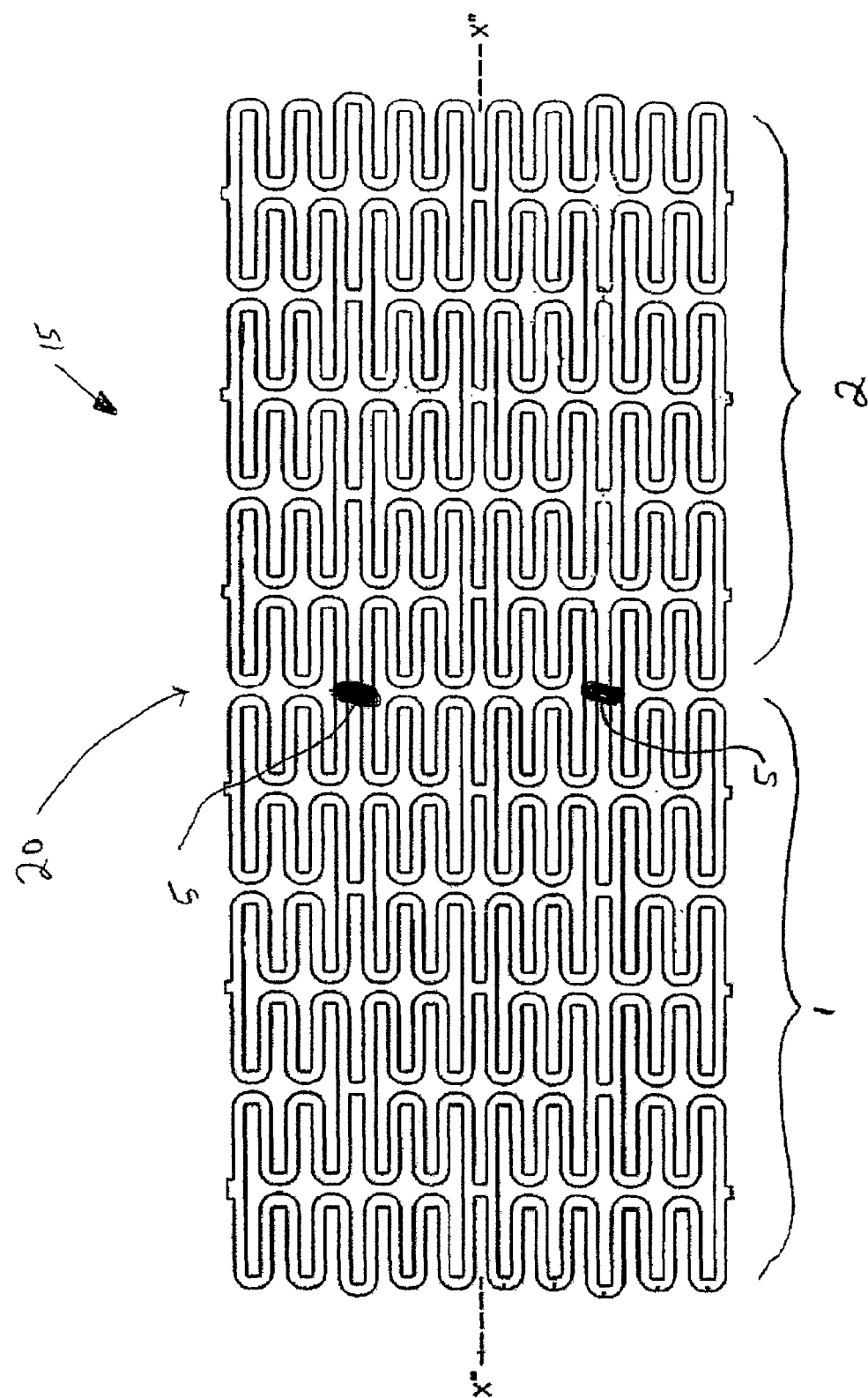
FIG. 8 is a schematic diagram of a stent in accordance with the present invention.

FIG. 7 illustrates another alternative embodiment of the inventive stent 15. In this embodiment, stent 15 comprises a balloon expandable segment 1 and a self expanding segment 2. The balloon expandable segment 1 is attached to the self expanding segment 2 at attachment region 20. The balloon and self expandable stent segments may be attached to each other so as to limit axial motion of one segment relative to the other. The stent segments can be attached to one another using means known in the art, including, but not limited to, mechanical interlock, welding, adhesive bonding, over molding, sintering, diffusion bonding, cladding, explosive bonding, ultrasonic welding. For example, a stent segment 1 comprising a titanium alloy can be welded to a stent segment 2 comprising Nitinol. FIG. 8 illustrates an example of implementation of the stent of FIG. 7. In FIG. 8, stent 15 comprises laser cut tubular stent segments 1 and 2 welded at attachment points 5 in attachment region 20. In FIG. 8, the longitudinal axis of stent 15 is indicated in the figure by dashed line "X."

Figure 9:
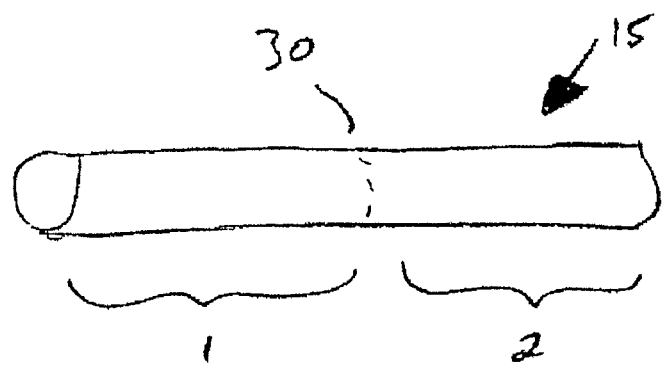
FIG. 9 illustrates conceptually a plan view of an alternate embodiment of a stent in accordance with the present invention.

FIG. 9 illustrates another alternative embodiment of a stent 15 having a singular piece of material to which different processes have been applied. As shown, stent 15 comprises stent segments 1 and 2 having different overall processing histories. For example, a body temperature superelastic nitinol stent may be heated in the region of stent segment 1 to raise the transition temperature in segment 1 to above body temperature, resulting in a balloon expandable stent segment 1 and a self expanding stent segment 2. Similarly an Elgiloy or cobalt-chrome alloy stent, initially heavily work hardened and self expanding, may be preferentially annealed to render a portion of the stent balloon expandable.

Figure 10:
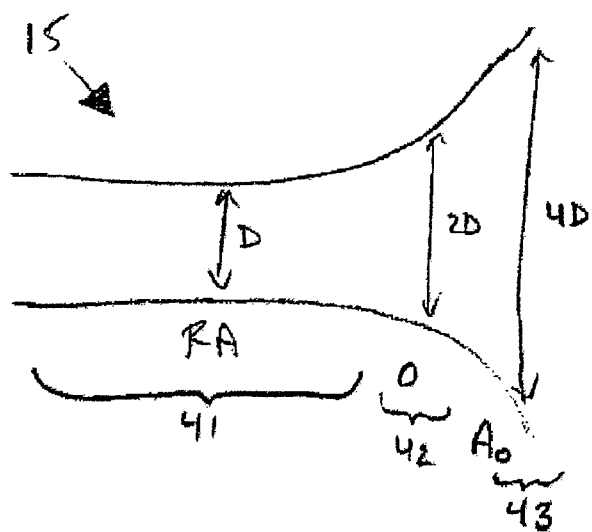
FIG. 10 illustrates conceptually the profile of a flared stent in accordance with the present invention.

FIG. 10 illustrates a side cut-away profile of another alternative embodiment of a stent 15 having cell designs with the same number of struts along its length. For example, in non-flared region 41 having stent diameter D, the stent struts have approximately 14-18% metal coverage area. In flared region 42 having stent diameter 2D, the stent struts have approximately 7-9% metal coverage area. In flared region 43 having stent diameter 4D, the stent struts have approximately 3.5-4.5% metal coverage area. It is known that stents having metal coverage area less than approximately 14-18% do not perform well due to tissue prolapse through the cells of the stent into the stented lumen, and due to potential extrusion of atheromatous material through the stent metal coverage area into the stented vessel lumen. To avoid sub-par stent performance in the stented and flared region, it is desirable to increase the metal coverage area to the approximately 15-18% range. One way to do this is by increasing the number of stent struts in region of the stent that will be flared as compared to the number of struts in the region of the stent that will not be flared.

Figure 11:
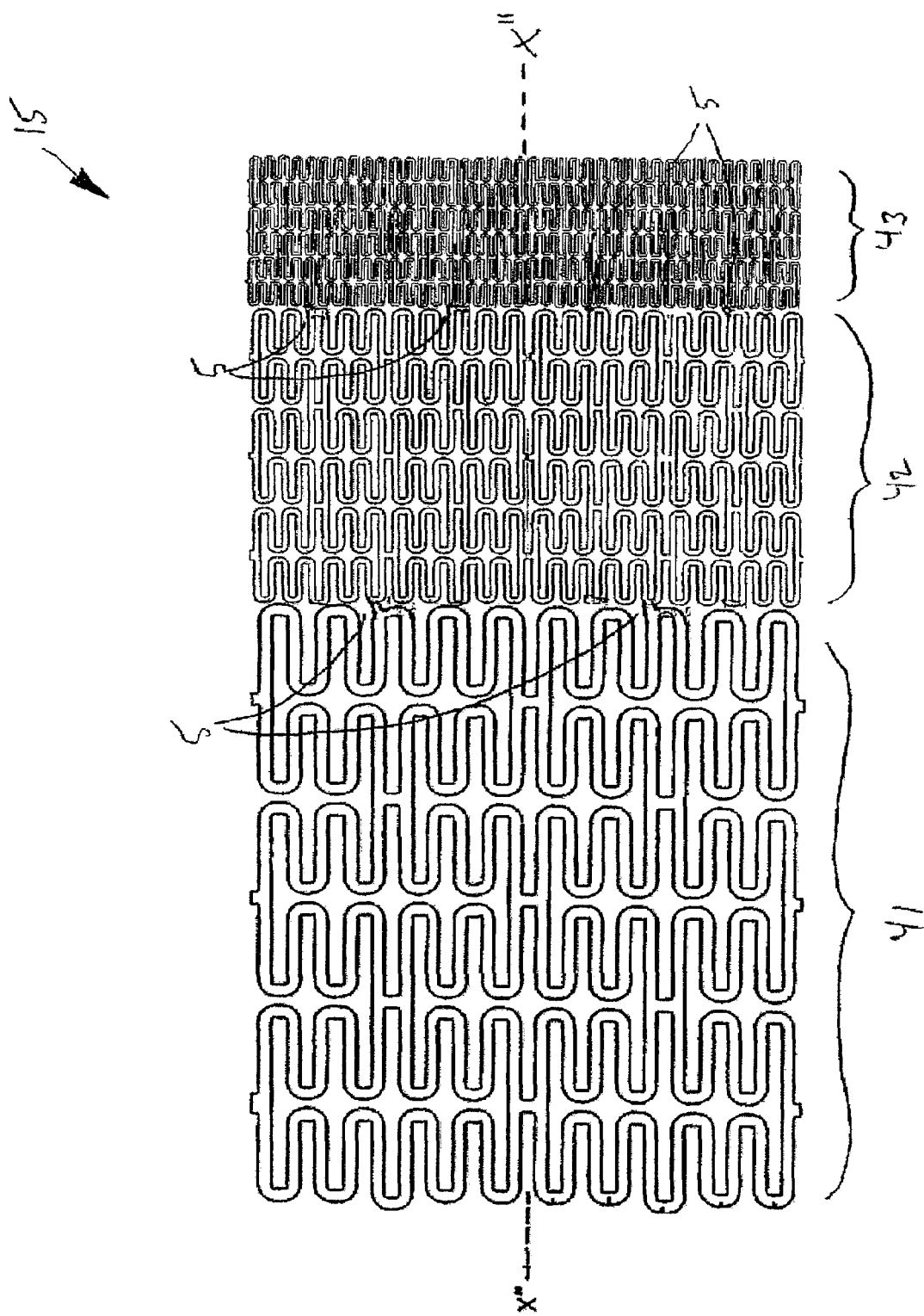
FIG. 11 is a schematic diagram of an alternate embodiment of a stent in accordance with the present invention.

FIG. 11 illustrates a stent embodiment for increasing the percent metal coverage area in the flared region of the deployed stent. In FIG. 11 the number of struts progressively increases in regions 41, 42, and 43 respectively. In FIG. 11 the compressed stent diameter is held constant while the compressed strut spacing varies in segments 41, 42, and 43. Attachment points between regions in this embodiment may comprise a laser cut tube segment, with the number of connecting struts increasing between adjacent segments as the density of the cell/strut configuration increases between adjacent segments. In one embodiment, segment 41 comprises 6 struts, segment 42 comprises 12 struts, and segment 43 comprises 24 struts. It is recognized that any number of struts and segments may be used to produce an overall stented region metal coverage area of a target value appropriate to the anatomy. For arteries the illustrative target metal coverage area is thought to be approximately 15-18%.

Figure 12:
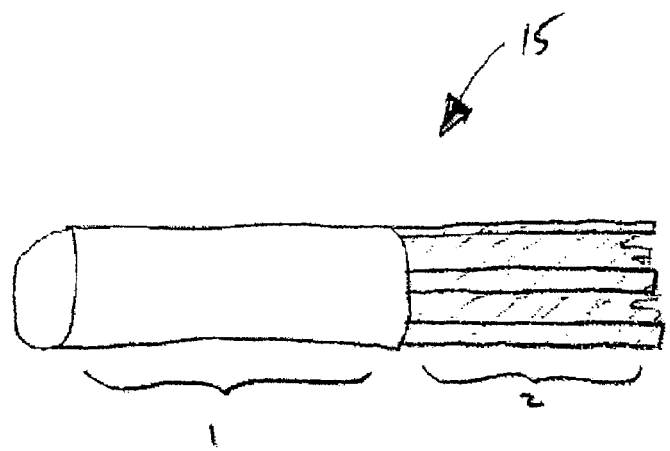
FIGS. 12 and 13 illustrate conceptually a plan view of another embodiment of a stent in accordance with the present invention.
Figure 13:
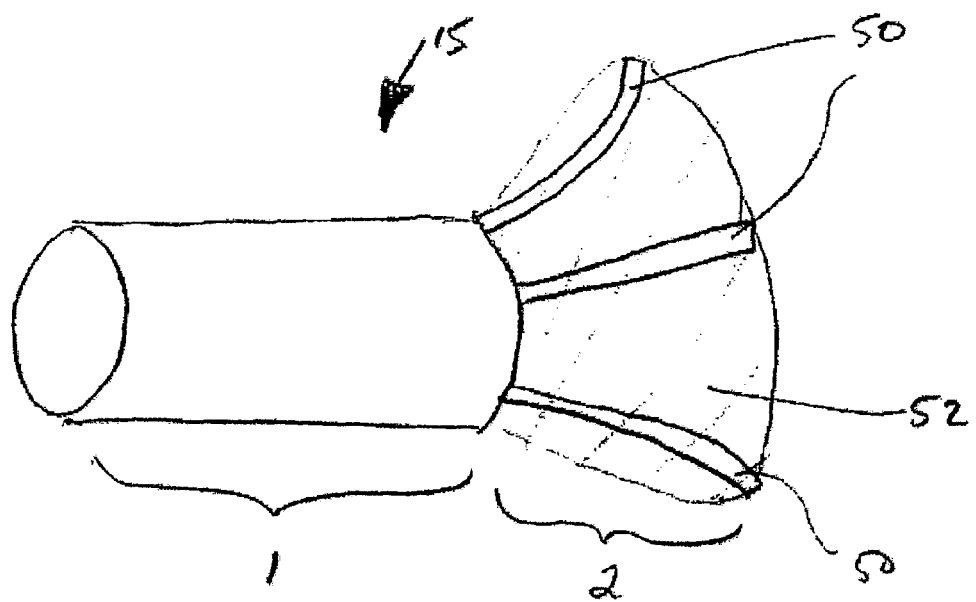
Figure 14:
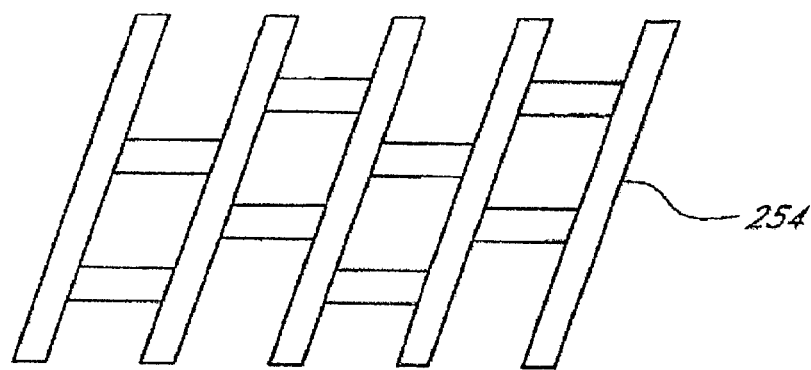
FIG. 14 is a schematic diagrams of a film material used in the stent embodiment of FIG. 17.

Another embodiment of stent 15 is illustrated in FIGS. 12 and 13. Stent 15 comprises balloon expandable segment 1 and self expanding segment 2. Balloon expandable segment 1 may have the construction and function similar any of the embodiments described herein. Self expandable segment 2 comprises leafs 50 and film 52. Leafs 50 comprise materials such as those described above for self expanding stent segment 2. Leafs 50 are attached to balloon expandable stent segment 1 using techniques similar to those described above regarding the embodiment of FIG. 7.

Film 52 is attached to leafs 50 by bonding. Film 52 may comprise any of a variety of membranous materials including those which facilitate cellular in-growth, such as ePTFE. The suitability of alternate materials for film 52 can be determined through routine experimentation. The film 52 may be provided on one or both radially facing sides of the leafs 50. In one embodiment, the film 52 comprises two layers, with one layer on each side of leafs 50. The two layers may be bonded to each other around the leafs using any of a variety of techniques, for example by heat bonding, with or without an intermediate bonding layer such as polyethylene or FEP, adhesives, sutures, or other techniques which will be apparent to those of recently skill in the arts in view of the disclosure herein. The film 52 preferably has a thickness of no more than about 0.006" and a pore size within the range of from approximately 5 μm to approximately 60 μm.

Film 52 in one embodiment preferably is securely attached to leafs 50 and retains a sufficient porosity to facilitate cellular ingrowth and/or attachment. One method of manufacturing a suitable composite membrane film 52 is illustrated in FIGS. 14-17. As illustrated schematically in FIG. 14, a bonding layer 254 preferably comprises a mesh or other porous structure having an open surface area within the range of from about 10% to about 90%. In one embodiment, the open surface area of the mesh is within the range of from about 30% to about 60%. The opening or pore size of the bonding layer 254 may be within the range of from about 0.005 inches to about 0.050 inches, and, in one embodiment, is about 0.020 inches. The thickness of the bonding layer 254 can be varied widely, and is generally within the range of from about 0.0005 inches to about 0.005 inches. In a illustrative embodiment, the bonding layer 254 has a thickness of about 0.001 to about 0.002 inches. One suitable polyethylene bonding mesh is commercially available from Smith & Nephew Inc., Memphis, Tenn. under the code SN9.

Figure 15:
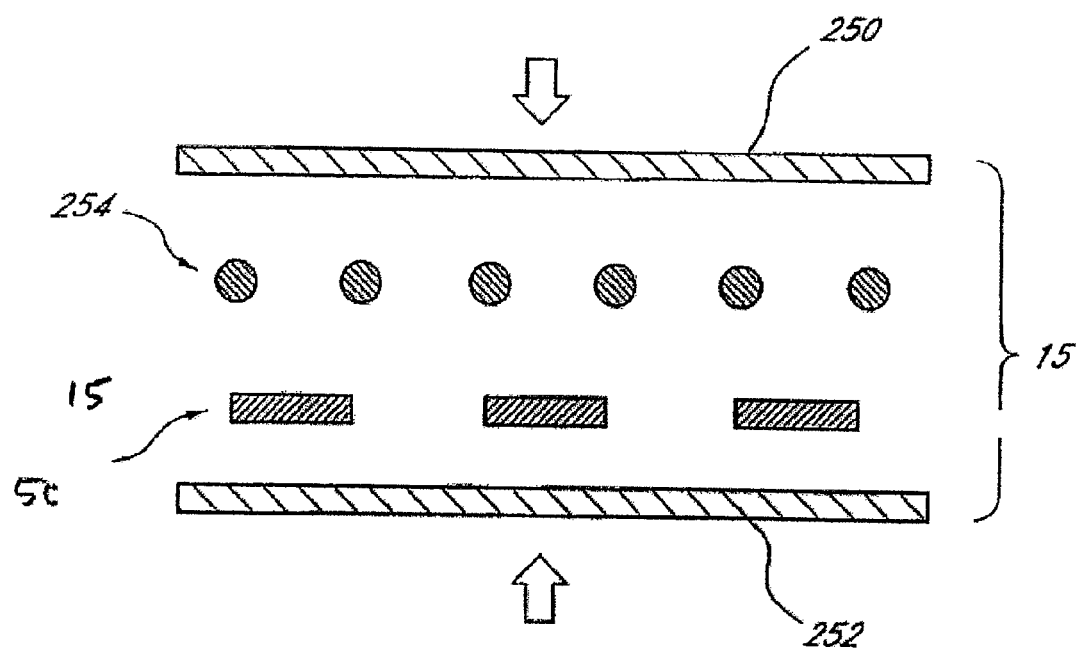
FIGS. 15 and 16 illustrate conceptually exploded and compressed cross-sectional diagram, respectively, of a film suitable for use with the stent embodiment of FIG. 17.

FIG. 15 is an exploded view illustrating the relationship between first membrane 250, second membrane 252, bonding layer 254 and leafs 50. Bonding layer 254 is disposed adjacent one or both sides of leafs 50. The bonding layer 254 and leafs 50 are then positioned in-between a first membrane 250 and a second membrane 252 to provide a composite membrane stack. The first membrane 250 and second membrane 252 may comprise any of a variety of materials and thicknesses, depending upon the desired functional result. Generally, the membrane has a thickness within the range of from about 0.0005 inches to about 0.010 inches. In one embodiment, the membranes 250 and 252 each have a thickness on the order of from about 0.001 inches to about 0.002 inches, and comprise porous ePTFE, having a pore size within the range of from about 10 microns to about 100 microns.

Figure 16:
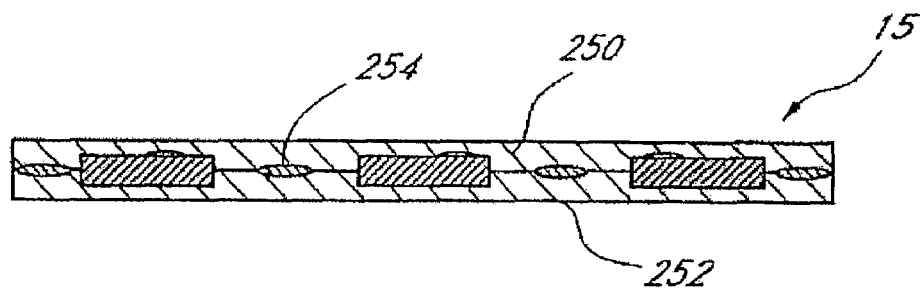

The composite stack is heated to a temperature of from about 200° F. to about 300° F., for about 1 minute to about 5 minutes under pressure to provide a finished composite membrane assembly with embedded leafs 50, as illustrated schematically in FIG. 16. The final composite membrane has a thickness within the range of from about 0.001 inches to about 0.010 inches, and, preferably, is about 0.002 to about 0.003 inches in thickness. However, the thicknesses and process parameters of the foregoing may be varied considerably, depending upon the materials of the bonding layer 254, first membrane 250, and second membrane 252.

Figure 17:
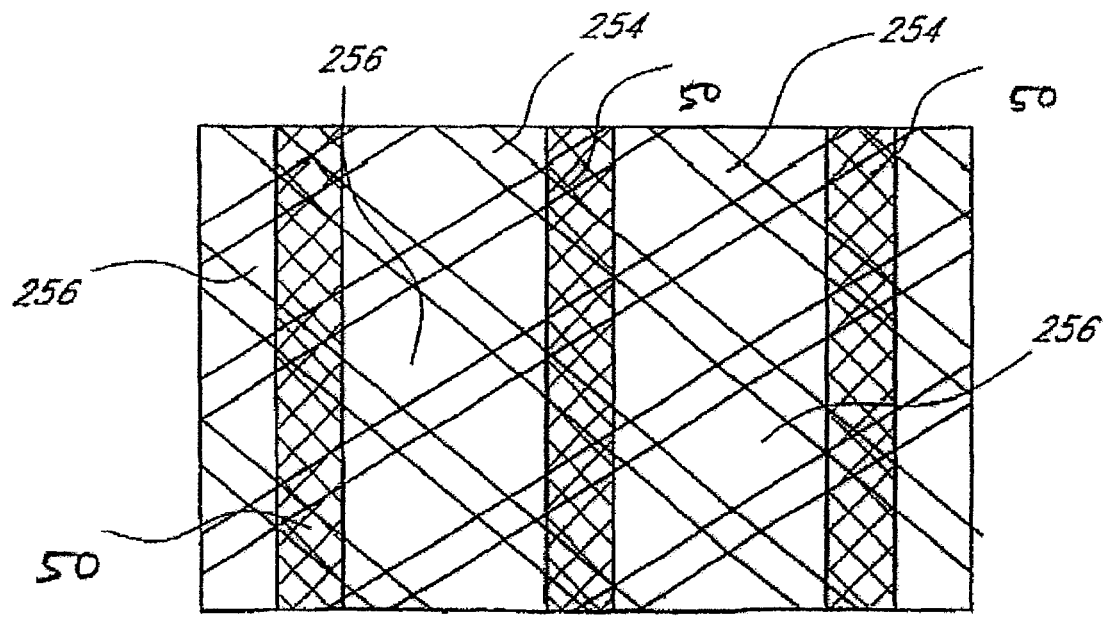
FIG. 17 illustrates conceptually a plan view of another embodiment of a stent in accordance with the present invention.

As illustrated in top plan view in FIG. 17, the resulting finished composite membrane film 52 has a plurality of "unbonded" windows or areas 256 suitable for cellular attachment and/or ingrowth. The attachment areas 256 are bounded by leafs 50, and the cross-hatch or other wall pattern formed by the bonding layer 254. Preferably, a regular window 256 pattern is produced in the bonding layer 254.

The foregoing procedure allows the bonding mesh to flow into the first and second membranes 250 and 252 and gives the composite membrane film 52 greater strength (both tensile and tear strength) than the components without the bonding mesh. The composite membrane allows uniform bonding while maintaining porosity of the membrane film 52, to facilitate tissue attachment. By flowing the thermoplastic bonding layer into the pores of the outer mesh layers 250 and 252, the composite flexibility is preserved and the overall composite layer thickness can be minimized. In another embodiment film 52 may be non-porous and comprise a polymer such as polyurethane or silicone.

A composite membrane film 52, when used in the stent embodiment illustrated in FIGS. 12-13, provides a barrier and prevents emboli from being shed from the stented region, when the self expanded segment 2 apposes ostial O and aortic Ao regions of a vessel.

While this document has described an invention mainly in relation to renal artery stenting, it is envisioned that the invention can be applied to other conduits in the body as well including arteries, veins, bronchi, ducts, ureters, urethra, and other lumens intended for the passage of air, fluids, or solids. The invention can be applied to any site of branching of an artery, vein, bronchus, duct, ureter, urethra, and other lumen including but not limited to the junction of the common, internal, and external carotid arteries, the junction of the main, left anterior descending, and circumflex coronary arteries, the junction of the left main or right coronary artery with the aorta, the junction of the aorta with the subclavian artery, and the junction of the aorta with the carotid artery.

While the various embodiments of the present invention have related to stents and stent delivery systems, the scope of the present invention is not so limited. Further, while choices for materials and configurations may have been described above with respect to certain embodiments, one of ordinary skill in the art will understand that the materials described and configurations are applicable across the embodiments.

What is claimed is:

1. A stent for insertion into a body lumen comprising:
    a first tubular, balloon-expandable section comprising a first plurality of struts within a unit of length measured circumferentially around a diameter of the stent in an unexpanded state;
    a second tubular, self-expanding section coupled to the first section and comprising a second plurality of struts within the unit of length that is greater than the first plurality of struts within the unit of length; and
    a third tubular, self-expanding section comprising a third plurality of struts within the unit of length that is greater than the number of struts within the unit of length in the second section,
    wherein a number of struts in the first section is selected to provide a metal coverage area of 14-18% in a balloon-expanded state of the first section inside the body lumen, and a number of struts in the second section is selected so that a metal coverage area is in a 15-18% range when the second section self-expands so that a diameter of the self-expanded second section is between about 2-times and 4-times greater than a diameter of the balloon-expanded first section, and a number of struts in the third section is selected so that a metal coverage area is in a 15-18% range when the third section self-expands so that a diameter of the self-expanded third section is between about 2-times and 4-times greater than a diameter of the balloon-expanded first section, so as to prevent tissue prolapse through open cells of the stent into the stented body lumen.

2. The stent of claim 1 wherein a strut of the second tubular section is coupled to a strut of the first tubular section by a process selected from the group consisting of mechanical interlock, welding, adhesive bonding, over molding, sintering, diffusion bonding, cladding, explosive bonding, and ultrasonic welding.

3. The stent of claim 1 in combination with a delivery system comprising:
    a catheter having a balloon carried at a distal end thereof;
    a proximal portion of the balloon having an expanded diameter greater than an expanded diameter of a more distal portion of the balloon.

4. The stent of claim 1 in combination with a delivery system comprising:
    a catheter having first and second balloons carried at a distal end thereof;
    a proximal of the balloons having an expanded diameter greater than an expanded diameter of a more distal of the balloons.

5. A method for placement of a medical device within a body lumen comprising:
    disposing a delivery system within the body lumen, the delivery system comprising:
    a tubular catheter having an outer shaft member slidably disposed about an inner shaft member;
    first and second balloons carried at a distal end of inner shaft member;
    a medical device comprising:
    a first balloon-expandable section disposed intermediate the first balloon and the outer shaft member, and
    a second self-expanding section disposed intermediate the second balloon and outer shaft member;
    withdrawing the outer shaft member proximally to expose the first balloon-expandable section of the medical device to the body lumen;
    inflating the first balloon to expand the first section of the medical device against the body lumen;
    withdrawing the outer shaft member proximally to expose the second self-expanding section of the medical device to the body lumen; and
    inflating the second balloon to expand the second section of the medical device at least partially against the body lumen.

6. The method of claim 5 wherein the body lumen is selected from the group consisting of coronary artery, ureter, urethra, bronchus, and esophagus.

* * * * *